United States Patent
Hosomi et al.

(10) Patent No.: US 9,982,110 B2
(45) Date of Patent: *May 29, 2018

(54) WATER-ABSORBING RESIN CROSSLINKING AGENT

(71) Applicant: Nagase ChemteX Corporation, Osaka-shi, Osaka (JP)

(72) Inventors: Tetsuya Hosomi, Hyogo (JP); Masato Fushiki, Hyogo (JP); Toyohiro Nagano, Hyogo (JP)

(73) Assignee: Nagase ChemteX Corporation, Osaka (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/123,899

(22) PCT Filed: Mar. 19, 2015

(86) PCT No.: PCT/JP2015/058257
§ 371 (c)(1),
(2) Date: Sep. 6, 2016

(87) PCT Pub. No.: WO2015/141780
PCT Pub. Date: Sep. 24, 2015

(65) Prior Publication Data
US 2017/0015808 A1    Jan. 19, 2017

(30) Foreign Application Priority Data

Mar. 19, 2014 (JP) ................. 2014-055851

(51) Int. Cl.
| | | |
|---|---|---|
| *C08K 5/053* | (2006.01) |
| *C08J 3/24* | (2006.01) |
| *A61L 15/60* | (2006.01) |
| *C08L 101/14* | (2006.01) |
| *A61L 15/22* | (2006.01) |
| *B01J 20/26* | (2006.01) |
| *C07C 31/36* | (2006.01) |
| *C07C 31/42* | (2006.01) |
| *C07C 41/03* | (2006.01) |
| *C07C 43/13* | (2006.01) |

(52) U.S. Cl.
CPC .............. *C08K 5/053* (2013.01); *A61L 15/22* (2013.01); *A61L 15/60* (2013.01); *B01J 20/267* (2013.01); *C07C 31/36* (2013.01); *C07C 31/42* (2013.01); *C07C 41/03* (2013.01); *C07C 43/137* (2013.01); *C08J 3/24* (2013.01); *C08J 3/245* (2013.01); *C08L 101/14* (2013.01); *C08J 2333/02* (2013.01); *C08J 2333/08* (2013.01)

(58) Field of Classification Search
CPC . C08K 5/053; B01J 20/267; C08J 3/24; C08J 3/245; C08J 2333/02; A61L 15/22; A61L 15/60
See application file for complete search history.

(56) References Cited

U.S. PATENT DOCUMENTS

| | | | |
|---|---|---|---|
| 2,260,753 | A | 10/1941 | Marple |
| 2002/0185629 | A1 | 12/2002 | Fujii et al. |
| 2009/0202805 | A1* | 8/2009 | Furno ..................... A61L 15/18 428/219 |
| 2011/0040044 | A1 | 2/2011 | Motoyama et al. |
| 2011/0301027 | A1* | 12/2011 | Bitis ....................... A61L 15/28 502/404 |

FOREIGN PATENT DOCUMENTS

| | | |
|---|---|---|
| CN | 102007170 A | 4/2011 |
| EP | 0 015 652 | 9/1980 |
| EP | 0 582 062 | 2/1994 |
| EP | 582062 A1 * | 2/1994 |

(Continued)

OTHER PUBLICATIONS https://web.archive.org/web/20120626155109/http://www.chemicalbook.com/ChemicalProductProperty_EN_CB22128636.htm, 2010.*
https://echa.europa.eu/information-on-chemicals/pre-registered-substances/-/dislist/substance/100.038.393; 2008.*
https://echa.europa.eu/information-on-chemicals/ec-inventory/-/dislist/substance/100.038.393; 2008.*
International Search Report issued for PCT/JP2015/058257, dated Jun. 23, 2015, 3 pages.

(Continued)

*Primary Examiner* — Roberto Rabago
(74) *Attorney, Agent, or Firm* — Hamre, Schumann, Mueller & Larson, P.C.

(57) ABSTRACT

The present invention aims to provide a water-absorbing resin crosslinking agent which is excellent in safety and which can effectively crosslink a water-absorbing resin at low temperatures to produce a water-absorbing agent having a high water absorption capacity. The present invention also aims to provide a water-absorbing agent produced by crosslinking a water-absorbing resin with the water-absorbing resin crosslinking agent, and a method for producing the water-absorbing agent. The present invention may include a water-absorbing resin crosslinking agent containing a halohydrin compound having one halohydrin group represented by the following formula (1) in its molecule:

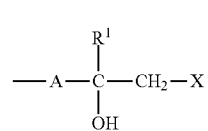

(1)

wherein A represents a single bond or an alkylene group; $R^1$ represents a hydrogen atom or an alkyl group; and X represents a chlorine atom or a bromine atom.

2 Claims, No Drawings

(56) References Cited

FOREIGN PATENT DOCUMENTS

| JP | 02-248404 | 10/1990 |
| JP | 2002-060544 | 2/2002 |
| JP | 2002-363340 | 12/2002 |
| JP | 2003-020363 | 1/2003 |
| WO | 2005/044915 | 5/2005 |

OTHER PUBLICATIONS

Novak et al. "Some observations on the reaction of ethylene glycol with 1-chloro-2,3-epoxypropane", Collection of Czechoslovak Chemical Communications, vol. 35, 1970, pp. 1096-1104.

* cited by examiner

WATER-ABSORBING RESIN CROSSLINKING AGENT

TECHNICAL FIELD

The present invention relates to a novel water-absorbing resin crosslinking agent which is excellent in safety and which can effectively crosslink a water-absorbing resin at low temperatures to produce a water-absorbing agent having a high water absorption capacity; and a method for producing the crosslinking agent. The present invention also relates to a water-absorbing agent produced by crosslinking a water-absorbing resin with the crosslinking agent.

BACKGROUND ART

Water-absorbing resins are widely used in various fields, including sanitary products, foods, agriculture and forestry industries, and civil engineering. These resins are generally used particularly in sanitary products such as paper diapers and sanitary napkins, taking advantage of their water absorption. Typical examples of such water-absorbing resins used in sanitary products include partially neutralized salts of polyacrylic acid or polymethacrylic acid.

Water-absorbing resins for use in sanitary products such as paper diapers are required to have a high water absorption capacity not only under normal pressure but also under body pressure (i.e. under pressure).

A possible known technical solution to the above problem is to crosslink the surface of water-absorbing resin particles with a crosslinking agent. In such a surface crosslinking method, the surface layers of water-absorbing resin particles containing a carboxylic acid group and/or a carboxylate group are crosslinked by a crosslinking agent while the water-absorbing resin particles are inhibited from being internally crosslinked in order to maintain the water absorption capacity, whereby a water-absorbing agent having a high water absorption rate can be obtained.

Conventionally, epoxy group-containing compounds have been used as such crosslinking agents. However, the crosslinking agents containing epoxy group-containing compounds may cause problems such as skin irritation. For this reason, crosslinking agents free of epoxy group-containing compounds have been proposed. Examples of these crosslinking agents include those containing compounds having at least two halohydrin groups in their molecule or compounds containing a halohydrin group and a quaternary ammonium group in their molecule (see Patent Literature 1). The examples also include crosslinking agents containing polyhydric alcohols having multiple amide backbones or oxazole backbones in their molecule (see Patent Literature 2). These crosslinking agents also provide water-absorbing resin particles with water absorption capacities comparable to those of the crosslinking agents containing epoxy group-containing compounds.

As described above, while various crosslinking agents that crosslink water-absorbing resin particles have been developed, recent improvements such as reduced thickness of sanitary products (e.g. paper diapers) have created a need for developing water-absorbing agents having higher water absorption capacity.

CITATION LIST

Patent Literature

Patent Literature 1: JP-A 2002-060544
Patent Literature 2: JP-A 2003-020363

SUMMARY OF INVENTION

Technical Problem

A main object of the present invention is to provide a novel water-absorbing resin crosslinking agent that can be used to produce a water-absorbing agent having a high water absorption capacity.

Solution to Problem

As a result of extensive studies, the present inventors have found that a water-absorbing agent having high water absorption can be produced with a water-absorbing resin crosslinking agent containing a compound having one halohydrin group in its molecule. The present invention was thus accomplished.

The water-absorbing resin crosslinking agent of the present invention may include, for example, the following agents.

[1] A water-absorbing resin crosslinking agent, containing a halohydrin compound having one halohydrin group represented by the following formula (1) in its molecule:

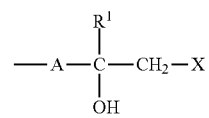

(1)

wherein A represents a single bond or an alkylene group; $R^1$ represents a hydrogen atom or an alkyl group; and X represents a chlorine atom or a bromine atom.

[2] The water-absorbing resin crosslinking agent according to Item [1], wherein the A is a methylene group.

[3] The water-absorbing resin crosslinking agent according to Item [1] or [2], wherein the halohydrin compound is a compound represented by the following formula (2):

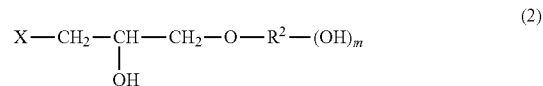

(2)

wherein $R^2$ represents a C2-C10 aliphatic hydrocarbon group having a valence of m+1; X represents a chlorine atom or a bromine atom; and m represents an integer of 0 to 4.

[4] A water-absorbing agent, produced by adding at least one water-absorbing resin crosslinking agent according to any one of Items [1] to [3] to a water-absorbing resin containing a carboxylic acid group and/or a carboxylate group, followed by heating to effect crosslinking.

[5] A method for producing a water-absorbing agent, the method including adding at least one water-absorbing resin crosslinking agent according to any one of Items [1] to [3] to a water-absorbing resin containing a carboxylic acid group and/or a carboxylate group, followed by heating.

Advantageous Effects of Invention

The water-absorbing resin crosslinking agent of the present invention is excellent in safety because it is free of functional groups that can irritate the skin, such as an epoxy group. Additionally, although the water-absorbing resin crosslinking agent contains a halohydrin compound having only one halohydrin group, it is possible, with such a crosslinking agent, to effectively crosslink a water-absorbing resin at low temperatures to produce a water-absorbing agent having a high water absorption capacity.

DESCRIPTION OF EMBODIMENTS

I. Water-Absorbing Resin Crosslinking Agent of the Present Invention

First, the water-absorbing resin crosslinking agent of the present invention (hereinafter referred to as "the crosslinking agent of the present invention") is described in detail.

I-1. Halohydrin Compound According to the Present Invention

The crosslinking agent of the present invention contains a halohydrin compound having one halohydrin group represented by the following formula (1) in its molecule:

wherein A represents a single bond or an alkylene group; $R^1$ represents a hydrogen atom or an alkyl group; and X represents a chlorine atom or a bromine atom.

$R^1$ is particularly preferably a hydrogen atom. When $R^1$ is an alkyl group, the "alkyl group" may be a C1-C3 alkyl group, for example. Specific examples include methyl, ethyl, and n-propyl groups, with a methyl group being preferred.

The "alkylene group" for A may be a C1-C4 alkylene group, for example. Specific examples include methylene, ethylene, propylene, and butylene groups, with a methylene group being preferred.

It is sufficient as long as the crosslinking agent of the present invention contains the halohydrin compound according to the present invention, optionally in admixture with another compound. Thus, the halohydrin group-containing compound in the crosslinking agent of the present invention may be the "halohydrin compound having one halohydrin group in its molecule according to the present invention" alone or may be in combination with a "compound having two or more halohydrin groups in its molecule".

The amount of the halohydrin compound according to the present invention in the crosslinking agent of the present invention is preferably 20 mol % or more, more preferably 40 mol % or more, still more preferably 90 mol % or more, based on the total halohydrin group-containing compound in the crosslinking agent of the present invention. When the halohydrin compound according to the present invention is within the range indicated above, the crosslinking agent of the present invention can be used to produce a water-absorbing agent having effectively increased water absorption capacity.

I-2. Specific Examples of Halohydrin Compound According to the Present Invention and Production Method Thereof Preferred specific examples of the halohydrin compound according to the present invention include a compound represented by the following formula (2):

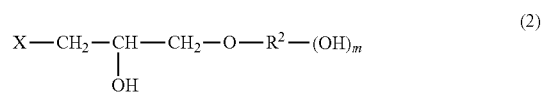

wherein $R^2$ represents a C2-C10 aliphatic hydrocarbon group having a valence of m+1; X represents a chlorine atom or a bromine atom; and m represents an integer of 0 to 4.

This halohydrin compound may be produced, for example, by reacting an m+1-hydric aliphatic alcohol with an epihalohydrin.

The m+1-hydric aliphatic alcohol is not particularly limited as long as it can react with an epihalohydrin. Specific examples include acyclic dihydric alcohols such as ethylene glycol, diethylene glycol, propylene glycol, triethylene glycol, tetraethylene glycol, 1,3-propanediol, dipropylene glycol, 2,2,4-trimethyl-1,3-pentanediol, 2-butene-1,4-diol, 1,3-butanediol, 1,4-butanediol, 1,5-pentanediol, and 1,6-hexanediol; acyclic trihydric alcohols such as glycerol and trimethylolpropane; acyclic tetrahydric alcohols such as pentaerythritol; cyclic alcohols such as 1,2-cyclohexanedimethanol and 1,2-cyclohexanediol; and ethanolamines such as diethanolamine and triethanolamine. Among these, acyclic dihydric to trihydric alcohols are preferred, with ethylene glycol, glycerol, and diethylene glycol being more preferred, and glycerol being particularly preferred. These may be used alone or in combination of two or more.

Examples of the epihalohydrin include epichlorohydrin and epibromohydrin, with epichlorohydrin being preferred for reasons such as easy availability. These may be used alone or in combination of two or more.

The reaction of the m+1-hydric aliphatic alcohol and the epihalohydrin can be carried out by conventional methods. Usually, a solvent may optionally be used for purposes such as control of the reaction or adjustment of the viscosity. Such a solvent is not particularly limited as long as it is inactive in the reaction of the m+1-hydric aliphatic alcohol and the epihalohydrin. Examples include aromatic hydrocarbons such as toluene and xylene; aliphatic hydrocarbons such as hexane and heptane; and ethers such as diethyl ether, diisopropyl ether, ethylene glycol dimethyl ether, diethylene glycol dimethyl ether, and dioxane. These may be used alone or in combination of two or more.

Additionally, a Lewis acid catalyst may be added as needed. The Lewis acid catalyst is not particularly limited as long as it allows the reaction to proceed smoothly. Examples include boron trifluoride ether complexes, tin tetrachloride, zinc borofluoride, titanium tetrachloride, zinc chloride, silica alumina, and antimony pentachloride. These may be used alone or in combination of two or more.

As for the amounts of the m+1-hydric aliphatic alcohol and of the epihalohydrin, it is appropriate that the epihalohydrin be used usually in an amount of 0.7 to 1.3 equivalents, preferably 0.9 to 1.1 equivalents, per equivalent of the m+1-hydric aliphatic alcohol. The use of the epihalohydrin in the range indicated above is preferred because there will not be a large amount of unreacted m+1-hydric aliphatic alcohol residues and the resulting product can crosslink a water-absorbing resin to produce a water-absorbing agent having a sufficient water absorption capacity.

Additionally, when the epihalohydrin is used in the range indicated above, the amount of unreacted epihalohydrin residues will be small and the resulting product can produce a water-absorbing agent excellent in safety.

The reaction temperature varies depending on the starting m+1-hydric aliphatic alcohol and epihalohydrin and other starting materials such as Lewis acid catalyst, but a reaction temperature in the range of 30° C. to 95° C. is appropriate. The reaction time varies depending on the starting m+1-hydric aliphatic alcohol and epihalohydrin and other starting materials such as Lewis acid catalyst, but a reaction time in the range of 1 hour to 8 hours is appropriate.

I-3. Crosslinking Agent of the Present Invention

With the crosslinking agent of the present invention, it is possible to effectively crosslink the surface of a water-absorbing resin containing a carboxylic acid group and/or a carboxylate group, which will be described later, to produce a water-absorbing agent having a high water absorption capacity. Thus, the crosslinking agent of the present invention can be suitably used as a surface-crosslinking agent for water-absorbing resins. Additionally, with the crosslinking agent of the present invention, it is also possible to internally crosslink the water-absorbing resin as needed.

The crosslinking agent of the present invention is preferably a crosslinking agent with which a water-absorbing agent can be produced by crosslinking a water-absorbing resin containing a carboxylic acid group and/or a carboxylate group with the crosslinking agent added at 2% by weight based on the water-absorbing resin, wherein the water-absorbing agent under a pressure of 50 g/cm² has a water absorption ratio of at least 20 times.

The "water-absorbing agent produced by crosslinking a water-absorbing resin containing a carboxylic acid group and/or a carboxylate group with the crosslinking agent added at 2% by weight based on the water-absorbing resin" may be any water-absorbing agent that can be produced with the crosslinking agent added at a feed ratio of 2% by weight of the water-absorbing resin. The amount of the crosslinking agent in the water-absorbing agent does not have to be 2% by weight of the water-absorbing resin.

The water-absorbing agent to be assessed as above may be produced by diluting the crosslinking agent (0.2 g in terms of solids) with water (1.0 g) to prepare an aqueous solution, and spraying the aqueous solution of the crosslinking agent to a water-absorbing resin containing a carboxylic acid group and/or a carboxylate group (10 g), such as polyacrylic acid, followed by sufficient mixing and then heating at 150° C. for 60 minutes.

The water absorption ratio is measured by the following method.

A crucible-shaped glass filter (inner diameter: 40 mm; height: 70 mm) is placed vertically, and the water-absorbing agent (1 g) to be assessed is placed uniformly therein. A PET film (thickness: 100 μm) is then put on the water-absorbing agent, and the initial weight is measured. Further, a weight having an outer diameter of 38 mm is put thereon to give a load of 50 g/cm². Subsequently, the crucible-shaped glass filter containing the water-absorbing agent to be assessed, with its bottom facing down, is immersed in a vat (length: 210 mm; width: 170 mm) containing 0.9% physiological saline (about 630 g) for 30 minutes. After immersion, the crucible-shaped glass filter is taken out, and an increase in the weight is measured. The increase in the weight is taken as the water absorption ratio.

When a water-absorbing agent is produced by crosslinking a water-absorbing resin containing a carboxylic acid group and/or a carboxylate group with the crosslinking agent added at 2% by weight based on the water-absorbing resin, the water absorption ratio of the water-absorbing agent under a pressure of 50 g/cm² is preferably at least 20 times, more preferably at least 25 times.

II. Water-Absorbing Agent of the Present Invention

Next, the water-absorbing agent produced with the crosslinking agent of the present invention (hereinafter referred to as "the water-absorbing agent of the present invention") is described in detail.

The water-absorbing agent of the present invention is produced by adding the crosslinking agent of the present invention to a water-absorbing resin containing a carboxylic acid group and/or a carboxylate group, followed by heating to effect crosslinking.

The water-absorbing agent of the present invention is usually produced by crosslinking the surface of a water-absorbing resin containing a carboxylic acid group and/or a carboxylate group with the crosslinking agent of the present invention. The water-absorbing resin may be internally crosslinked in some cases. Such a water-absorbing agent internally crosslinked by the crosslinking agent of the present invention is also included in the present invention.

II-1. Surface Crosslinking

The case where the surface of a water-absorbing resin containing a carboxylic acid group and/or a carboxylate group is crosslinked with the crosslinking agent of the present invention is described.

The water-absorbing resin containing a carboxylic acid group and/or a carboxylate group is not particularly limited as long as it contains a carboxylic acid group and/or a carboxylate group and absorbs water and swells to form a hydrogel. For example, any known water-absorbing resin may be used. Specific examples include crosslinked, partially neutralized polyacrylic acids, self-crosslinked, partially neutralized polyacrylic acids, crosslinked starch-acrylate graft copolymers, hydrolysates of crosslinked starch-acrylonitrile graft copolymers, crosslinked vinyl alcohol-acrylate copolymers, crosslinked acrylate-acrylamide copolymers, hydrolysates of crosslinked acrylate-acrylonitrile copolymers, and crosslinked copolymers of acrylates and 2-acrylamido-2-methylpropanesulfonates. These may be used alone or in combination of two or more.

Among the examples of the water-absorbing resin, water-absorbing resins containing a carboxylic acid group and/or a carboxylate group at a high density are preferred because they have high water absorption capacities. Specific examples of such water-absorbing resins include crosslinked, partially neutralized polyacrylic acids and self-crosslinked, partially neutralized polyacrylic acids. Examples of carboxylates include sodium salts, potassium salts, and ammonium salts, with sodium salts being particularly preferred.

The production method and shape of the water-absorbing resin containing a carboxylic acid group and/or a carboxylate group are not particularly limited. Examples include a reverse phase suspension polymerization method and pearl-like water-absorbing resin particles produced by this method; and an aqueous solution polymerization method and water-absorbing resins having a scale-like, bulky, rock-like, granular, or amorphous shape produced by drying and crushing of polymers formed by this method. The examples also include pellets formed from these water-absorbing resin particles.

When surface crosslinking is carried out with the crosslinking agent of the present invention, although the amount of the crosslinking agent of the present invention varies depending on the type and degree of crosslinking of the water-absorbing resin and the intended degree of surface crosslinking, the amount thereof may be adjusted such that the amount of the halohydrin compound in the crosslinking agent of the present invention to be used is usually 0.01 to 20 parts by weight, preferably 0.05 to 10 parts by weight, more preferably 0.1 to 5 parts by weight, relative to 100 parts by weight of the water-absorbing resin. When the amount of the halohydrin compound in the crosslinking agent of the present invention to be used relative to 100 parts by weight of the water-absorbing resin is within the range indicated above, not only can the water-absorbing resin be effectively crosslinked, but also a decrease in the water absorption capacity or water absorption rate of the resulting water-absorbing agent, which can occur due to an excessive increase in the crosslink density, can be prevented.

In the surface crosslinking of the water-absorbing resin by the crosslinking agent of the present invention, preferably the crosslinking agent of the present invention is dissolved in advance in water, a hydrophilic organic solvent, or a mixed solvent of these solvents before the thus-obtained solution containing the crosslinking agent of the present invention is mixed with the water-absorbing resin. Examples of the hydrophilic organic solvent include lower aliphatic alcohols such as methanol, ethanol, n-propyl alcohol, and isopropyl alcohol; ketones such as acetone; ethers such as dioxane, tetrahydrofuran, and methoxy(poly)ethylene glycol; amides such as ε-caprolactam and N,N-dimethylformamide; sulfoxides such as dimethyl sulfoxide; and polyhydric alcohols such as ethylene glycol, diethylene glycol, propylene glycol, triethylene glycol, tetraethylene glycol, polyethylene glycol, 1,3-propanediol, dipropylene glycol, polypropylene glycol, glycerol, and polyglycerol. These hydrophilic organic solvents may be used alone, or two or more of these may be combined into a mixed solvent.

The amount of the hydrophilic organic solvent to be used may be adjusted appropriately according to the type and particle size of the water-absorbing resin, water content, and other factors, but it is usually 0.1 to 20 parts by weight, preferably 0.5 to 10 parts by weight, relative to 100 parts by weight of solids of the water-absorbing resin.

The crosslinking agent of the present invention and the water-absorbing resin may be mixed together by a known method using a cylindrical mixer, V-shaped mixer, ribbon type mixer, screw mixer, double arm mixer, grinding kneader, or other devices, for example, after the solution containing the crosslinking agent of the present invention is sprayed to the water-absorbing resin. In the mixing, a surfactant may be added as needed.

A known surface-crosslinking agent may also be used in combination to an extent that does not impair the surface-crosslinking effect of the crosslinking agent of the present invention. Examples of the known surface-crosslinking agent include polyhydric alcohol compounds, polyvalent amine compounds, polyisocyanate compounds, polyvalent oxazoline compounds, alkylene carbonate compounds, silane coupling agents, and polyvalent metal compounds. Further, epoxy compounds or haloepoxy compounds may also be used in combination.

Examples of the polyhydric alcohol compounds include ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanediol, trimethylolpropane, diethanolamine, triethanolamine, polyoxypropylene, oxyethylene-oxypropylene block copolymers, pentaerythritol, and sorbitol.

Examples of the epoxy compounds include ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol.

Examples of the polyvalent amine compounds include ethylenediamine, diethylenetriamine, triethylenetetramine, tetraethylenepentamine, pentaethylenehexamine, polyethyleneimine, and inorganic or organic salts (e.g. azitinium salts) of these polyvalent amine compounds.

Examples of the polyisocyanate compounds include 2,4-tolylene diisocyanate and hexamethylene diisocyanate. Examples of the polyvalent oxazoline compounds include 1,2-ethylenebisoxazoline.

Examples of the alkylene carbonate compounds include 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, and 4,6-dimethyl-1,3-dioxan-2-one.

Examples of the haloepoxy compounds include epichlorohydrin, epibromohydrin, α-methylepichlorohydrin, and polyvalent amine adducts thereof (Kymene (Registered Trademark) available from Hercules Inc.).

Examples of other known crosslinking agents include silane coupling agents such as γ-glycidoxypropyltrimethoxysilane and γ-aminopropyltriethoxysilane; and polyvalent metal compounds such as hydroxides and chlorides of zinc, calcium, magnesium, aluminium, iron, zirconium, or other metals.

These known surface-crosslinking agents may be used alone or in combination of two or more.

The heating temperature during the surface crosslinking may vary appropriately according to the type of crosslinking agent of the present invention, the type of water-absorbing resin, and other factors, but it is usually 40° C. to 250° C. When the heating temperature is within the range indicated above, the surface of the water-absorbing resin particles can be uniformly crosslinked, without degradation of the water-absorbing resin particles, to produce a water-absorbing agent having an excellent balance between water absorption ratio under normal pressure and water absorption ratio under pressure and a high water absorption capacity.

However, since the crosslinking agent of the present invention is highly reactive, it allows a surface crosslinking reaction to occur rapidly and uniformly even at a relatively low heating temperature. Accordingly, the heating temperature is preferably 60° C. to 200° C., more preferably 70° C. to 200° C.

The heating time may also be adjusted appropriately according to the type of crosslinking agent of the present invention, the type of water-absorbing resin, and other factors, but it is usually 0.2 hours to 3 hours.

The water-absorbing agent of the present invention may contain other additives to impart various functions. Examples of such additives include disinfectants, deodorants, antibacterial agents, perfumes, various inorganic powders, foaming agents, pigments, dyes, hydrophilic short fibers, fertilizers, oxidizing agents, reducing agents, water, and salts. The amounts of these other additives and the timing of addition thereof can be selected appropriately by a person skilled in the art.

EXAMPLES

The present invention is described in further detail below with reference to examples, but the present invention is by no means limited to these examples. In the following description, "%" indicates "% by weight".

(Water Absorption Ratio Under Pressure of Water-Absorbing Agent)

The water absorption performance under pressure of water-absorbing agents produced by crosslinking a water-absorbing resin with a crosslinking agent of the present invention (water-absorbing agents of the present invention) was assessed as follows.

A crucible-shaped glass filter (inner diameter: 40 mm; height: 70 mm) was placed vertically, and the water-absorbing agent (1 g) was placed uniformly therein. A PET film (thickness: 100 μm) was then put on the water-absorbing agent, and the initial weight Wa (g) was measured. Further, a weight having an outer diameter of 38 mm was put thereon to give a load of 50 g/cm². Subsequently, the crucible-shaped glass filter containing the water-absorbing agent, with its bottom facing down, was immersed in a vat (length: 210 mm; width: 170 mm) containing 0.9% physiological saline (about 630 g) for 30 minutes. After immersion, the crucible-shaped glass filter was taken out, and the weight after water absorption Wb (g) was measured. The water absorption ratio under pressure was calculated from these Wa and Wb values using the following equation.

Water absorption ratio under pressure=$(Wb(g)-Wa(g))$/Weight of water-absorbing agent $(g)$ (Examples of Crosslinking Agents of the Present Invention)

Example 1

Ethylene glycol (50 g, 0.8 mol) and a boron trifluoride ether complex (0.3 g) as a catalyst were fed to a 300 mL separable flask, followed by heating and stirring. Epichlorohydrin (74.5 g, 0.8 mol) was added dropwise thereto while the internal temperature was maintained at 50° C. to 60° C. When the dropwise addition was finished, the reaction system formed a homogeneous solution. After the completion of the dropwise addition, the reaction system was stirred at the same temperature as above, and the reaction was finished when the disappearance of epichlorohydrin was confirmed based on the quantification of epoxy groups by titration. After the completion of the reaction, ion-exchanged water (1.4 g) was added in the same temperature range to give a crosslinking agent of the present invention (A1) containing a halohydrin compound represented by formula (2) where X is a chlorine atom, $R^2$ is an ethylene group, and m=1.

Example 2

Glycerol (200 g, 2.2 mol) and tin tetrachloride (0.9 g) as a catalyst were fed to a 1 L separable flask, followed by heating and stirring. Epichlorohydrin (221 g, 2.4 mol) was added dropwise thereto while the internal temperature was maintained at 70° C. to 75° C. When the dropwise addition was finished, the reaction system formed a homogeneous solution. After the completion of the dropwise addition, the internal temperature was raised to 90° C. to 95° C. and stirring was continued in the same temperature range, and the reaction was finished when the disappearance of epichlorohydrin was confirmed based on the quantification of epoxy groups by titration. After the completion of the reaction, ion-exchanged water (280 g) and a 48.7% sodium hydroxide aqueous solution (0.3 g) were added in the same temperature range, and the solvent was removed by vacuum concentration. Isopropyl alcohol (281 g) was added to the concentrated residue, followed by filtration to give a crosslinking agent of the present invention (A2) containing a halohydrin compound represented by formula (2) where X is a chlorine atom, $R^2$ is an isopropylene group, and m=2.

Reference Example 1

Glycerol (220 g, 2.4 mol) and a boron trifluoride ether complex (0.3 g) as a catalyst were fed to a 300 mL separable flask, followed by heating and stirring. Epichlorohydrin (486 g, 5.3 mol) was added dropwise thereto while the internal temperature was maintained at 50° C. to 55° C. When the dropwise addition was finished, the reaction system formed a homogeneous solution. After the completion of the dropwise addition, the reaction system was stirred at the same temperature as above, and the reaction was finished when the disappearance of epichlorohydrin was confirmed based on the quantification of epoxy groups by titration. After the completion of the reaction, ion-exchanged water (235 g) and a 48.7% sodium hydroxide aqueous solution (0.2 g) were added in the same temperature range, and the solvent was removed by vacuum concentration. Isopropyl alcohol (471 g) was added to the concentrated residue, followed by filtration to give a crosslinking agent (A3) containing a halohydrin compound having two halohydrin groups in its molecule, represented by formula (1) where A is a methylene group, $R^1$ is a hydrogen atom, and X is a chlorine atom.

(Examples of Water-Absorbing Agents of the Present Invention (Surface-Crosslinking Water-Absorbing Resin Particles))

Example 3

The crosslinking agent of the present invention (A1) (0.1 g in terms of solids) produced in Example 1 was diluted with water (0.5 g) to prepare an aqueous solution (1%/water-absorbing resin particles). Likewise, the crosslinking agent of the present invention (A1) (0.2 g in terms of solids) was diluted with water (1.0 g) to prepare an aqueous solution (2%/water-absorbing resin particles).

Each crosslinking agent aqueous solution was sprayed to polyacrylate water-absorbing resin particles (10 g), followed by mixing. The thus-treated water-absorbing resin particles were heated at 150° C. for 60 minutes to give a water-absorbing agent of the present invention. Table 1 shows the performance of the thus-obtained water-absorbing agents of the present invention.

Example 4

Water-absorbing agents of the present invention were produced in the same manner as in Example 3, except that the crosslinking agent of the present invention (A2) produced in Example 2 (0.1 g and 0.2 g, respectively, in terms of solids) was used instead of the crosslinking agent of the present invention (A1). Table 1 shows their performance.

Comparative Example 1

Water-absorbing agents were produced in the same manner as in Example 3, except that the crosslinking agent (A3) produced in Reference Example 1 (0.1 g and 0.2 g, respectively, in terms of solids) was used instead of the crosslinking agent of the present invention (A1). Table 1 shows their performance.

TABLE 1

|  | Crosslinking agent | Water absorption ratio (1%/water-absorbing resin particles) | Water absorption ratio (2%/water-absorbing resin particles) |
|---|---|---|---|
| Example 3 | A1 | 16.6 | 21.4 |
| Example 4 | A2 | 18.5 | 25.6 |
| Comparative Example 1 | A3 | 13.6 | 19.1 |

As is clear from Table 1, the water-absorbing agents of the present invention produced with the crosslinking agents of the present invention have high water absorption ratios.

INDUSTRIAL APPLICABILITY

The crosslinking agent of the present invention is excellent in safety and which can effectively crosslink a water-absorbing resin at low temperatures. Accordingly, the water-absorbing agent produced with the crosslinking agent of the present invention (the water-absorbing agent of the present invention) exhibits a high water absorption capacity and thus is useful in the field of sanitary products such as paper diapers.

The invention claimed is:

1. A water-absorbing agent, produced by adding at least one water-absorbing resin crosslinking agent to a water-absorbing resin comprising a carboxylic acid group and/or a carboxylate group followed by heating to effect crosslinking, the water-absorbing resin crosslinking agent comprising:

a halohydrin compound represented by the following formula (2):

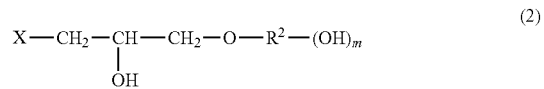

wherein $R^2$ represents a C2-C10 aliphatic hydrocarbon group having a valence of m+1, X represents a chlorine atom or a bromine atom, and m represents an integer of 0 to 4.

2. A method for producing the water-absorbing agent according to claim 1, the method comprising:
adding the at least one water-absorbing resin crosslinking agent to the water-absorbing resin; and
heating the at least one water-absorbing resin crosslinking agent and the water absorbing resin.

* * * * *